US010006897B1

(12) United States Patent
Ensign et al.

(10) Patent No.: US 10,006,897 B1
(45) Date of Patent: Jun. 26, 2018

(54) DEVICES FOR MEASURING PARAMETERS OF WATER

(71) Applicant: Scott Howard Ensign, Morehead City, NC (US)

(72) Inventors: Scott Howard Ensign, Morehead City, NC (US); Ryan Neve, Morehead City, NC (US)

(*) Notice: Subject to any disclaimer, the term of this patent is extended or adjusted under 35 U.S.C. 154(b) by 200 days.

(21) Appl. No.: 14/666,257

(22) Filed: Mar. 23, 2015

Related U.S. Application Data

(60) Provisional application No. 61/971,785, filed on Mar. 28, 2014, provisional application No. 62/062,913, filed on Oct. 12, 2014.

(51) Int. Cl.
G01N 33/18 (2006.01)

(52) U.S. Cl.
CPC ......... G01N 33/18 (2013.01); G01N 33/1886 (2013.01)

(58) Field of Classification Search
CPC ...... G01N 33/1886; G01N 33/18; B63G 8/22; B63G 8/14
See application file for complete search history.

(56) References Cited

U.S. PATENT DOCUMENTS

| 5,007,285 A | 3/1991 | Dahlen et al. |
| 5,007,364 A | 4/1991 | Buckle |
| 5,283,767 A | 2/1994 | McCoy |
| 6,544,088 B1 * | 4/2003 | Dubois ................... B63B 22/24 441/6 |
| 6,772,705 B2 | 8/2004 | Leonard et al. |
| 7,290,496 B2 * | 11/2007 | Asfar ..................... B63G 8/001 114/312 |
| 7,559,236 B1 * | 7/2009 | Lapota ............... G01N 33/1886 73/170.29 |
| 7,690,247 B1 | 4/2010 | Lapota et al. |
| 7,921,795 B2 * | 4/2011 | Imlach ..................... B63G 8/22 114/331 |
| 8,069,808 B1 | 12/2011 | Imlach et al. |

(Continued)

FOREIGN PATENT DOCUMENTS

EP 2392922 A1 12/2011

Primary Examiner — Paul West
Assistant Examiner — Xin Zhong
(74) Attorney, Agent, or Firm — NK Patent Law, PLLC

(57) ABSTRACT

A portable device for measuring parameters of water includes: a shield spherical in shape; an instrument capsule maintaining a water-tight seal with the shield, isolating water inside the shield from water outside the shield; electronic sensors extending from the capsule for measuring chemical, physical, hydrological, and/or biological properties of water; a computer control device within the capsule for programming operation and data storage for the electronic sensors; a battery within the instrument capsule for powering the electronic sensors and computer control device; an electronic signal generator to transmit an acoustic or radio signal into water surrounding the instrument capsule; an electronic signal receiver to receive an acoustic signal in water surrounding the instrument capsule; a supply of compressed gas within the instrument capsule; an assembly capable of trapping gas released from the instrument capsule; and a valve capable of connecting the supply of compressed gas within the assembly.

7 Claims, 13 Drawing Sheets

(56) References Cited

U.S. PATENT DOCUMENTS

| | | | |
|---|---|---|---|
| 8,381,672 B1* | 2/2013 | Eriksen | B63G 8/22 |
| | | | 114/125 |
| 8,397,658 B1 | 3/2013 | Imlach et al. | |
| 2003/0227394 A1* | 12/2003 | Rothgeb | A47L 15/4297 |
| | | | 340/870.01 |
| 2005/0084419 A1* | 4/2005 | Hill | G01N 1/14 |
| | | | 422/68.1 |
| 2005/0166826 A1* | 8/2005 | Marion | B63B 43/12 |
| | | | 114/312 |
| 2005/0207939 A1 | 9/2005 | Roussi et al. | |
| 2012/0312215 A1* | 12/2012 | Lyons | B63C 7/10 |
| | | | 114/54 |
| 2013/0068011 A1 | 3/2013 | Van Mooy et al. | |
| 2013/0083624 A1* | 4/2013 | Brizard | B63C 11/42 |
| | | | 367/15 |
| 2015/0177212 A1* | 6/2015 | Thomas | G01C 13/00 |
| | | | 114/331 |

* cited by examiner

DEVICES FOR MEASURING PARAMETERS OF WATER

CROSS-REFERENCE TO RELATED APPLICATION

This application claims the benefit of priority of U.S. provisional patent application No. 61/971,785, titled "ELECTRONIC SENSOR DEVICE AND MESOCOSM CHAMBER FOR MEASUREMENT OF ENVIRONMENTAL CHARACTERISTICS ALONG FLOW PATHS IN STREAMS, RIVERS, LAKES, AND ESTUARIES," filed on Mar. 28, 2014, which is incorporated herein in its entirety by this reference. This application also claims the benefit of priority of U.S. provisional patent application No. 62/062,913, titled "WATER TRACKING DEVICE WITH OPTIONAL SENSORS AND MESOCOSM CHAMBER FOR MEASURING WATER MOVEMENT, ENVIRONMENTAL CHARACTERISTICS, AND ENVIRONMENTAL PROCESSES IN WATER," filed on Oct. 12, 2014, which is incorporated herein in its entirety by this reference.

TECHNICAL FIELD

This relates to the measurement of water movement, environmental parameters, and biological, biogeochemical, and ecological processes in streams, rivers, lakes, reservoirs, and estuaries

BACKGROUND

Environmental parameters, including but not limited to, dissolved gases, chemical compounds, solute concentrations, organisms, and ecological communities, are measured to analyze the condition of aquatic and estuarine environments. Measurements are made using a variety of techniques which can be broadly classified as either synoptic ("snapshots" at a single point in time) or continuous (high frequency measurements over an extended time). Continuous measurement of environmental parameters can be conducted in reference to a fixed location (such as a moored buoy or bridge), in reference to a moving object (such as a vessel), or in reference to a moving parcel of water (such as flowing water in an ocean, river, lake, or estuary).

Portions of the current discussion pertain to environmental parameters being measured in synchrony with the movement of water. Measurement of environmental parameters in synchrony with the movement of water allows measurement of how parameters change along a discrete flow path of water.

In addition to measuring environmental parameters along the flow path of a stream, river, lake, reservoir, or estuary, it is sometimes also the objective of researchers to measure changes in those parameters within a controlled volume of water over time. For example, common experiments include measuring the uptake of nutrients by algae or the degradation of a chemical compound under controlled conditions that simulate some aspect of the natural environment (e.g., sunlight, temperature, fish).

Experiments require a chamber for holding a volume of water and its associated constituents in which measurements of an environmental parameter can be made over time. The chamber isolates the water inside from surrounding water, but may be designed to allow exchange of selected solutes or a size range of particles in the surrounding water. In order to measure these processes along a flow path of water, the chamber should be designed to travel freely with the water surrounding it.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

The objectives described above may be accomplished by specialized equipment. The physical design may minimize the risk of being snagged by submerged debris (e.g., branches, trees, weeds, human refuse) in a river, lake or estuary. Also, the design may minimize being trapped within physical features of the water body itself, such as shallow areas and eddy pools.

The design may provide a uniform surface for water currents and turbulence to act on, such that the movement of water in three dimensions is translated into equal forces acting on the instrument in three dimensions. In other words, the movement of the instrument may mirror the movement of the water surrounding it so that the instrument's path traces a discrete flow path of water in the environment. Thus the design may maximize the influence of water currents while minimizing the influence of wind or waves at the water surface.

The design may allow for the continual measurement of its location, either autonomously or by a remote operator. Knowledge of the location of the device is critical to analyzing how environmental parameters change in relation to the flow path of water. The design should allow continual measurement of the geographic location of the device and/or allow a person to continually locate the device using radio or acoustic tracking. The design may also allow a person to monitor the geographic location of the device remotely using cellular phone and/or satellite communication networks to transmit location information. Knowledge of the device's path of travel helps in analyzing how environmental parameters change in relation to the flow of water the device is embedded in.

An option related to the design is that it may allow for either deployment and travel strictly at the surface of the water or travel subsurface. A method can be accomplished with neutral or negative buoyancy, and provides the advantage of avoiding debris on the surface of the water and accidental strikes from passing vessels. Furthermore, subsurface travel allows measurement of Lagrangian transport in three dimensions: laterally, vertically, and horizontally. This may provide a unique advantage for researching biological, biogeochemical, and ecological processes in rivers, streams, lakes, reservoirs, and estuaries.

In at least one aspect, a device and/or method provides the ability to measure environmental parameters along a flow path of water in rivers, lakes, and estuaries. The device may contain a variety of electronic sensors for measuring environmental parameters. It may be generally spherical in shape to minimize the risk of being snagged by underwater debris. A spherical shape also projects a uniformly-shaped surface for turbulent forces to act on it from all directions, which allows more accurate measurement of the hydrologic environment. The device may also be used to incubate a volume of water by isolating it from the water surrounding it. The device can be located while submerged and tracked using manual or autonomous radio frequency or acoustic signaling and receiving systems. The device can be triggered to float to the surface by a remote signal from the operator or can self-activate its flotation. In various embodiments the positive, neutral, or negative buoyancy of the device can be determined by an operator before deployment or can be autonomously regulated by an on-board computer-controlled system.

In at least one aspect, a device and/or method provides the ability to continuously measure the geographic path of a drifting device along the course of a stream, river, lake, reservoir, or estuary. The path may include subsurface drifting in which the device is neutrally or negatively buoyant. In addition, a person can incubate a volume of water and its associated constituents inside the device so that water remains wholly or partially isolated from the water surrounding the device. This provides a person the ability to perform research on a controlled volume of water entrained within a moving body of water. Also provided is the ability to measure environmental parameters in the surrounding water and/or within the incubated volume of water inside the device. The shape of the device minimizes influence by wind and waves, maximizes influence by water currents, and minimizes the risk of becoming snagged by debris on the banks or bottom of the water body. A person may track the device as it moves by detecting a radio frequency and/or acoustic signal emitted from the device. Additionally, the device is equipped with a Global Positioning System (GPS) receiver that measures and records the geographic position of the device and may relay that information to a person via cellular phone (Global System for Mobile Communication, GSM) and/or satellite communication networks. The device may also transmit data collected by sensors on the device to a person via GSM and/or satellite communication networks. If submerged during travel, the device has a means to positively change its buoyancy so that it floats to the surface for recovery.

In at least one embodiment, a portable device for measuring environmental parameters of water bodies includes: a shield that is generally spherical in shape; an instrument capsule that is inserted into and connected with the shield, maintaining a water-tight seal with the shield, thereby isolating water inside the shield from water outside the shield; a plurality of electronic sensors extending from the instrument capsule for measuring one or more of chemical, physical, hydrological, and biological properties of water; a computer control device/module contained within the instrument capsule for programming the operation of and data storage from the electronic sensors; a battery contained within the instrument capsule for powering the electronic sensors and computer control device; an electronic signal generator that can transmit an acoustic or radio signal into water surrounding the instrument capsule; an electronic signal receiver that can receive an acoustic signal in water surrounding the instrument capsule; a supply of compressed gas contained within the instrument capsule; an inflatable device attached to the instrument capsule; and a valve within the instrument capsule that is capable of connecting the supply of compressed gas within the instrument capsule with the inflatable device.

In at least one example, a volume of the instrument capsule is adjustable by: an actuator within the instrument capsule that can adjust the volume of the instrument capsule by extending or retracting one end of the instrument capsule; and a computer control device that controls the actuator.

In at least one example, the instrument capsule extends across a diameter of the shield, allowing the electronic sensors to contact water outside of the shield.

In at least one embodiment, a portable device for measuring environmental parameters of water bodies includes: a shield that is generally spherical in shape and has multiple apertures to allow the free exchange of water between an inside and outside of the shield; an instrument capsule that is inserted into and connected with the shield; a plurality of electronic sensors extending from the instrument capsule for measuring one or more of chemical, physical, hydrological, and biological properties of water; a computer control device contained within the instrument capsule for programming the operation of and data storage from the electronic sensors; a battery contained within the instrument capsule for powering the electronic sensors and computer control device; an electronic signal generator that can transmit an acoustic or radio signal into water surrounding the instrument capsule; an electronic signal receiver that can receive an acoustic signal in water surrounding the instrument capsule; a supply of compressed gas contained within the instrument capsule; an inflatable device attached to the instrument capsule; and a valve within the instrument capsule that is capable of connecting the supply of compressed gas within the instrument capsule with the inflatable device.

In at least one embodiment, a portable device for conducting environmental studies in streams, rivers, lakes, reservoirs, and estuaries includes a generally spherical shell that provides a surface for water currents to act on and reduces the risk of said device being snagged on debris that would inhibit free movement in water; means for adding a volume of water and its associated constituents to an internal chamber of the shell and storing the volume of water and associated constituents such that they remain partially or wholly isolated from water surrounding the shell; means for adding or subtracting ballast or flotation to the shell so as to control the buoyancy and orientation of the device in water; a water-tight chamber within the shell containing electronic components selected from the group consisting of a GPS, a radio signal transmitter, an acoustic signal transmitter, a GSM Transceiver, a satellite communications transceiver, and a computer processor; a means for electronically connecting said electronic components with one another and with a battery; and antennas for said electronic components extending from the opposite side of the shell from the ballast so as to permit the antennas to extend above a water's surface when the portable device is positively buoyant.

In at least one example, the electronic components include sensors for measuring environmental characteristics of water surrounding the shell.

In at least one example, wherein a volume of compressed air can be expelled into the spherical shell when the portable device is submerged and thereby change the buoyancy of the portable device from negative or neutral to positive.

In at least one example, the electronic components include sensors for measuring environmental characteristics of water inside the volume of water and its associated constituents.

In at least one example, a volume of compressed air may be expelled into the said spherical shell when the portable device is submerged and thereby change the buoyancy of the portable device from negative or neutral to positive.

BRIEF DESCRIPTION OF THE DRAWINGS

The previous summary and the following detailed descriptions are to be read in view of the drawings, which illustrate particular exemplary embodiments and features as briefly described below. The summary and detailed descrip

DETAILED DESCRIPTIONS

Figure 1:
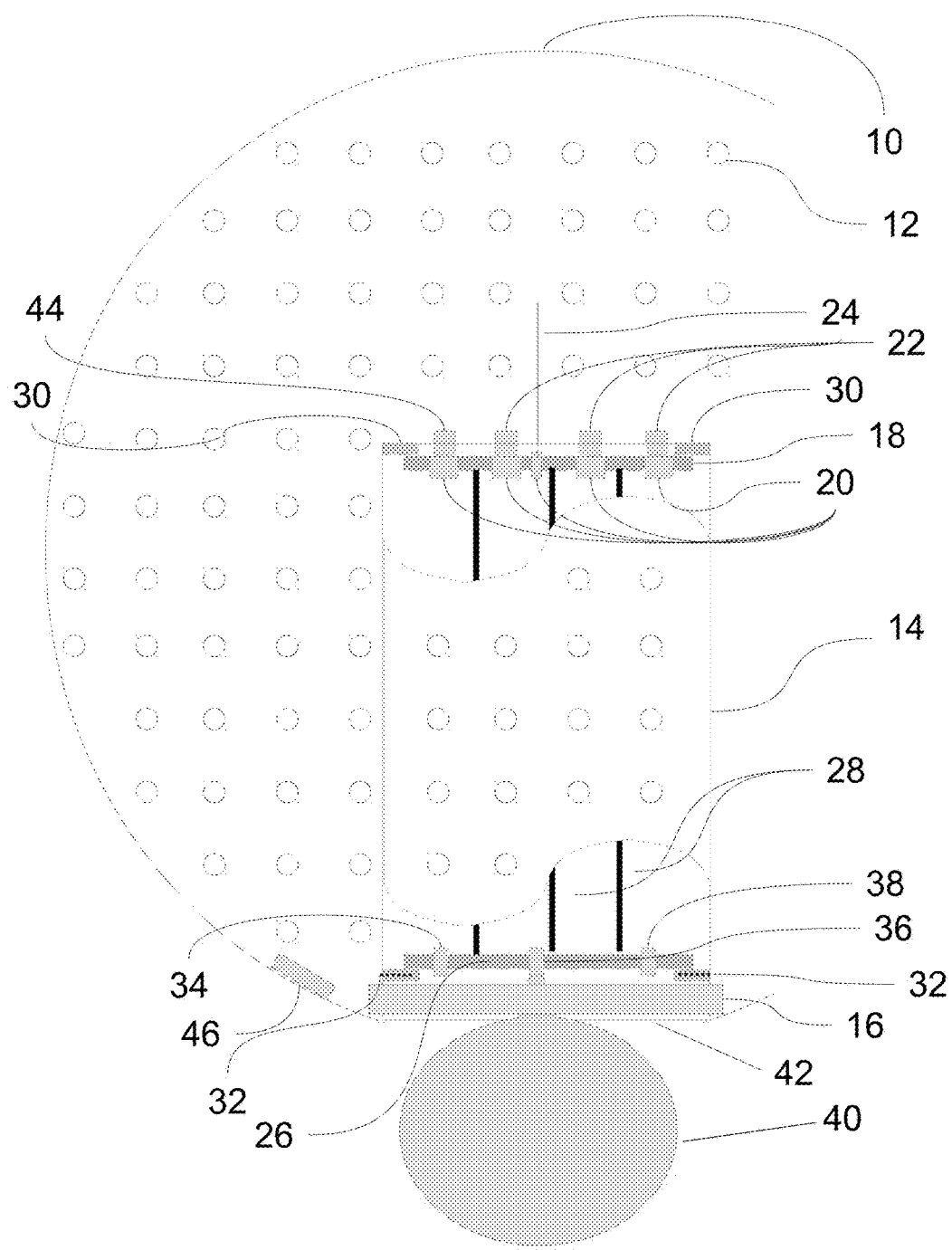
- FIG. 1 is a cutaway side view of a device, according to at least one embodiment, showing the configuration of the shield and instrument capsule.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

In FIGS. 1-6, reference numbers refer to features as follows:
10—shield
12—holes
14—instrument capsule
16—bottom collar
18—top end cap
20—fittings
22—sensors
24—electronic signal generator and transmitter
26—bottom end cap
28—support struts
30—retainer flange
32—detachable retainer ring
34—electrical connection port
36—gas port
38—gas valve
40—inflatable device
42—recess
44—acoustic signal receiver
46—magnets
48—computer control device/module
50—battery
52—gas solenoid
54—tubing
56—processor
58—memory unit
60—wireless communication device
62—internal pressure sensor
64—accelerometer
66—compass
68—o-rings
70—electronics assembly
72—actuator
74—seals
76—top collar The electric sensors are provided for measuring one or more of chemical, physical, hydrological, and biological properties of water. In one or more embodiments, a non-electrical based sensor may be employed.

Embodiment of FIGS. 1-4

One embodiment of the instrument is illustrated in FIGS. 1-4. Referring first to FIG. 1, a spherical shield 10 is perforated with holes 12, the diameter of which can vary depending on application-specific requirements. Shield 10 may be constructed of various kinds of clear plastic or metal depending on the specific requirements of the aquatic or marine habitat being studied. While generally spherical in shape, shield 10 has an aperture at the bottom to allow insertion of an instrument capsule 14. Instrument capsule 14 is inserted into shield 10 and the two are connected using bottom collar 16. Extruding from top end cap 18 are a plurality of liquid-tight through-hull penetration fittings 20, each allowing a sensor 22 to pass through top end cap 18. A variety of sensors 22 may be used, including but not limited to sensors for measuring temperature, conductivity, pH, dissolved oxygen, carbon dioxide, nitrate, irradiance, and pressure. The orientation of sensors and their associated fittings 20 may be modified as necessary to accommodate the number of sensors required for specific research. An electronic signal generator and transmitter 24 are also passed through one of said fittings 20.

The bottom end cap 26 is connected to top end cap 18 by a plurality of support struts 28. Retainer flange 30 prevents top end cap 18 from extruding out of instrument capsule 14, and a detachable retainer ring 32 keeps bottom end cap 26 secured into instrument capsule 14. Detachable retainer ring 32 is secured inside instrument capsule 14 using bolts. Electrical connection port 34, gas port 36, and gas valve 38 all pass through bottom end cap 26. Inflatable device 40 is connected to gas port 36, and is stored inside recess 42 when deflated.

An acoustic signal receiver 44 exits top end cap 18 through one of said fittings 20. Around the aperture at the bottom of shield 10 are magnets 46 which can be used to temporarily attach metal ballast.

Figure 2:
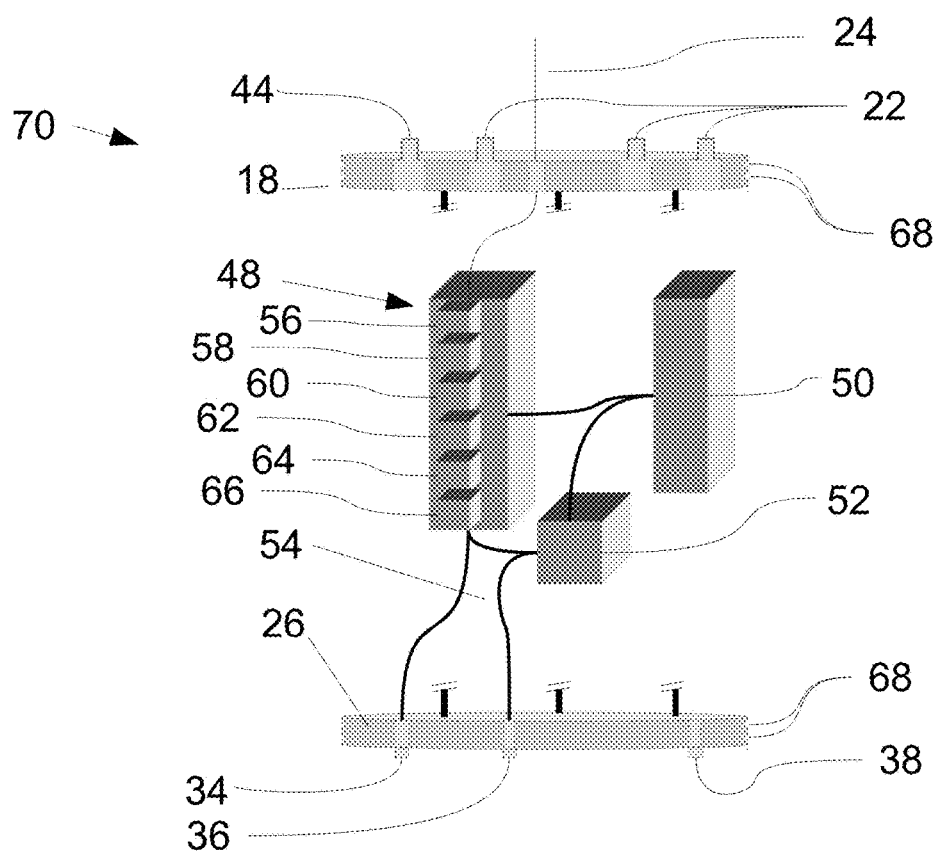
FIG. 2 is a side view of an electronics assembly, according to at least one embodiment, that fits within the instrument capsule of FIG. 1.
Figure 3:
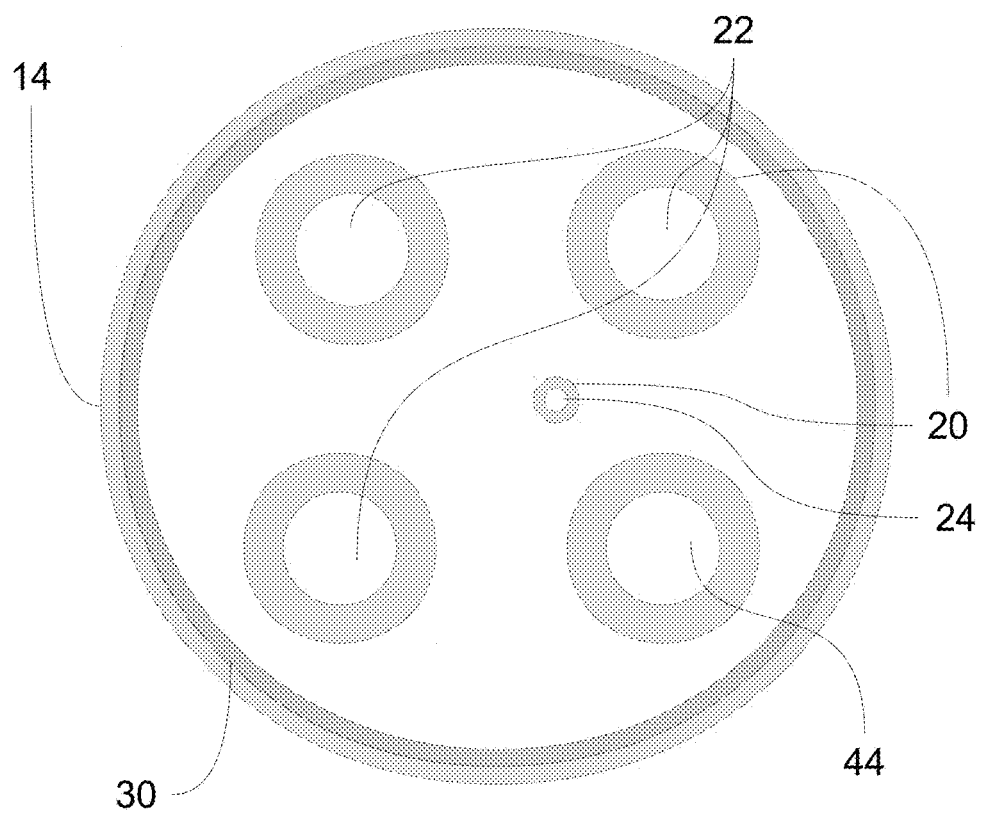
FIG. 3 is a top view of the instrument capsule of FIG. 1 and the electronics assembly of FIG. 2.

Now referring to FIG. 2, a computer control device 48 is electrically connected to sensors 22, electronic signal generator 24, acoustic signal receiver 44, and electrical connection port 34. A battery 50 is connected to electrical connection port 34 and supplies power to the computer control device 48, electronic signal generator 24, and acoustic signal receiver 44. A gas solenoid 52 is connected to computer control device 48 and battery 50. Tubing 54 provides communication of air between gas solenoid 52 and inflatable device 40 via gas port 36. Computer control device 48 is comprised of a processor 56, memory unit 58, wireless communication device 60, internal pressure sensor 62, accelerometer 64, and compass 66. O-rings 68 form a water-tight seal against the interior wall of instrument capsule 14 when electronics assembly 70 is inserted into instrument capsule 14.

Computer control device 48 can interrogate sensors 22 at pre-programmed intervals or in response to particular information received from the sensors, and store this information in memory unit 58. Accelerometer 64 measures the acceleration in three dimensions and is therefore useful for determining the strength of hydrologic forces acting on shield 10. Wireless communication device 60 and electrical connection port 34 both enable connection of an external computer with computer control device 48. Electrical connection port 34 also allows connection of an external power source to battery 50 for charging.

Now referring to FIG. 2, electronic signal generator and transmitter 24 broadcasts an acoustic or electromagnetic signal through the water which can be detected by an operator on shore or in a vessel using a hand-held receiver, allowing the operator to determine the position of the device.

Still referring to FIG. 2, computer control device 48 triggers gas solenoid 52 to open, thereby allowing communication of air inside instrument capsule 14 with inflatable device 40. Computer control device 48 can trigger gas solenoid 52 based on a pre-programmed time or by a signal communicated to computer control device 48 by acoustic signal receiver 44. An operator on shore or in a vessel can use a hand-held transmitter to signal acoustic signal receiver 44.

Figure 4:
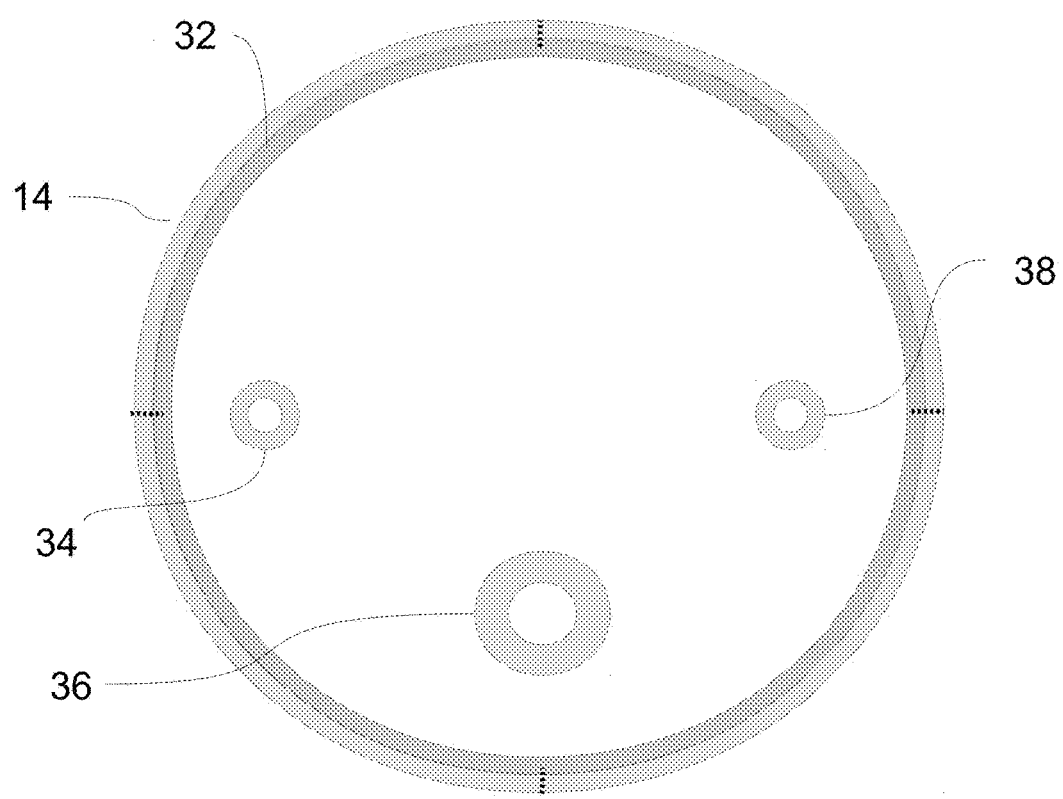
FIG. 4 is a bottom view of the instrument capsule and electronics assembly of FIG. 3.

Referring now to FIG. 4, gas valve 38 allows connection of an external pressure or vacuum source to instrument capsule 14.

Operation—Embodiment of FIGS. 1-4

The operational overview of the embodiment of the instrument of FIGS. 1-4 is provided next. There are three main stages of operation: 1) pre-deployment preparations; 2) deployment; 3) retrieval.

Pre-deployment preparations include procedures to: 1) program computer control device 48; 2) calibrate sensors 22; 3) pressurize instrument capsule 14. Computer control device 48 is programmed to read or interrogate electrical output of the sensors 22 at defined intervals and log the data to memory unit 58. This programming is performed by connecting an external computer to the computer control device 48 via electrical connection port 34 or wireless communication device 60. Also during this programming, computer control device 48 may be programmed to control gas solenoid 52 at a set time or when computer control device 48 receives a signal from one or more sensors 22. For example, computer control device 48 may be instructed to open the gas solenoid 52 after 5 days of deployment or when a salinity of 5 is measured. Finally, computer control device 48 is programmed to control the frequency and period at which electronic signal generator and transmitter 24 transmits a signal.

The next stage of pre-deployment preparations includes the calibration of the sensors. Sensors such as dissolved oxygen or salinity must be calibrated using standard solutions and procedures. These procedures are carried out according to the specifications of the sensor's manufacturers.

The last stage of pre-deployment preparations involves pressurizing instrument capsule 14. This involves three steps: 1) inserting and securing electronics assembly 70 into instrument capsule 14; 2) evacuation of gas from inflatable device 40; and 3) pressurization of instrument capsule 14. The first step of inserting and securing electronics assembly 70 into instrument capsule 14 requires ensuring that o-rings 68 are in place. After inserting electronics assembly 70, detachable retainer 32 is bolted into the inside bottom edge of instrument capsule 14. Next, gas is evacuated from inflatable device 40. This step involves first connecting an external computer to computer control device 48 and instructing computer control device 48 to open gas solenoid 52. Next, an external vacuum is connected to the gas valve 38, and the pressure inside instrument capsule 14 is reduced to the extent that air in the inflatable device 40 is completely evacuated. Computer control device 48 is then instructed to close gas solenoid 52, and the vacuum supply is removed from gas valve 38. Finally, an external compressed gas supply is applied to gas valve 38. Measurements from internal pressure sensor 62 are relayed through computer control device 48 to an external computer while the operator monitors the pressure until the working pressure is achieved. The minimum working pressure of instrument capsule 14 is determined by the highest ambient pressure the device will experience during deployment. This ambient pressure is a function of the maximum depth of water the device will encounter during deployment.

Following the pre-deployment preparations described above the device is ready to be deployed. In preparation for deployment, the temperature and salinity of the water body are measured. These data are used to calculate the density of water using standard formulas. Next, the mass of the device is adjusted so that its density (mass per volume) will equal the density of water it will be deployed in. As used herein, density will typically refer to the envelope density of the device, meaning the total density of the device as determined as the sum of the mass of the device and mass of fluid within the device and the volume that the device occupies. The mass of the device can be adjusted by a combination of adding small increments of ferrous metal weights to magnets 46 and by adding or releasing gas from instrument capsule 14 via gas valve 38. It is assumed that the volume of the device has previously been determined by the operator using standard methods. Once the desired buoyancy of the device has been achieved, the device is released into the water.

Following the deployment of the device, an operator may track the position of the device using a radio frequency receiver or hydroacoustic receiver tuned to the frequency of electronic signal generator and transmitter 24. The position of the device may also be monitored using an autonomous network of hydroacoustic receivers. To retrieve the device from a surface vessel, the operator actuates a hydroacoustic projector using a frequency and period that acoustic signal receiver 44 can detect and relay to computer control device 48. When acoustic signal receiver 44 detects the signal, computer control device 48 opens gas solenoid 52 which fills inflatable device 40 with air. This action floats the device to the surface for the operator to retrieve. As an alternative to the operator signaling the device manually, computer control device 48 may be pre-programmed to open gas solenoid 52 at a specific time.

Figure 5:
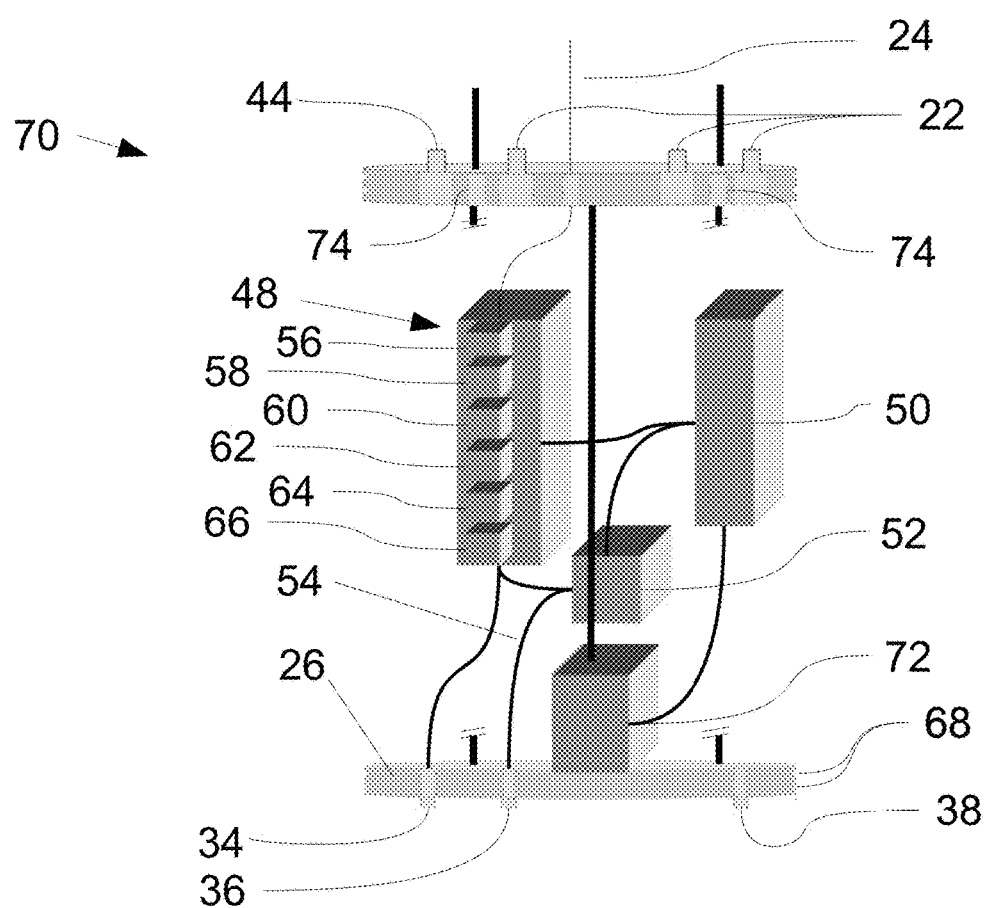
FIG. 5 is a side view of another embodiment of an instrument capsule showing mechanical actuator and sliding top end cap.

Embodiment of FIG. 5

Another embodiment of the device is shown in FIG. 5. A mechanical actuator 72 is connected to support struts 28 and bottom end cap 26. Mechanical actuator 72 can extend and retract top end cap 18, thereby changing the volume of water displaced by instrument capsule 14. Mechanical actuator 72 is electrically connected to and controlled by computer control device 48. Extension and refraction of mechanical actuator 72 slides top end cap 18 along support struts 28. Seals 74 are held within top end cap 18 and provide a water-proof connection for support struts 28 to slide through.

Operation—Embodiment of FIG. 5

Similarly to the embodiment of FIGS. 1-4, there are three main stages of operation: 1) pre-deployment preparations; 2) deployment; 3) retrieval. In addition to these stages of operation, the embodiment shown in FIG. 5 requires programming computer control device 48 with an algorithm for controlling mechanical actuator 72. The algorithm relies on instantaneous measurements by sensors 22 of temperature and salinity of the water surrounding the device in order to calculate the density of water surrounding the device. The algorithm also requires a mathematical relationship between the volume of water displaced by the instrument capsule and the extension of mechanical actuator 72. Given the density of water surrounding the device, the relationship between position of mechanical actuator 72 and the device's displacement of water, and a constant mass of the device, computer control device 48 uses the algorithm to determine the position of mechanical actuator 72 that is necessary for the density of the device to equal the density of the surrounding water. Continuous input of temperature and salinity from probes 22 into computer control device 48 results in continuous positioning of mechanical actuator 72 to maintain the desired buoyancy (positive, neutral, or negative).

Figure 6:
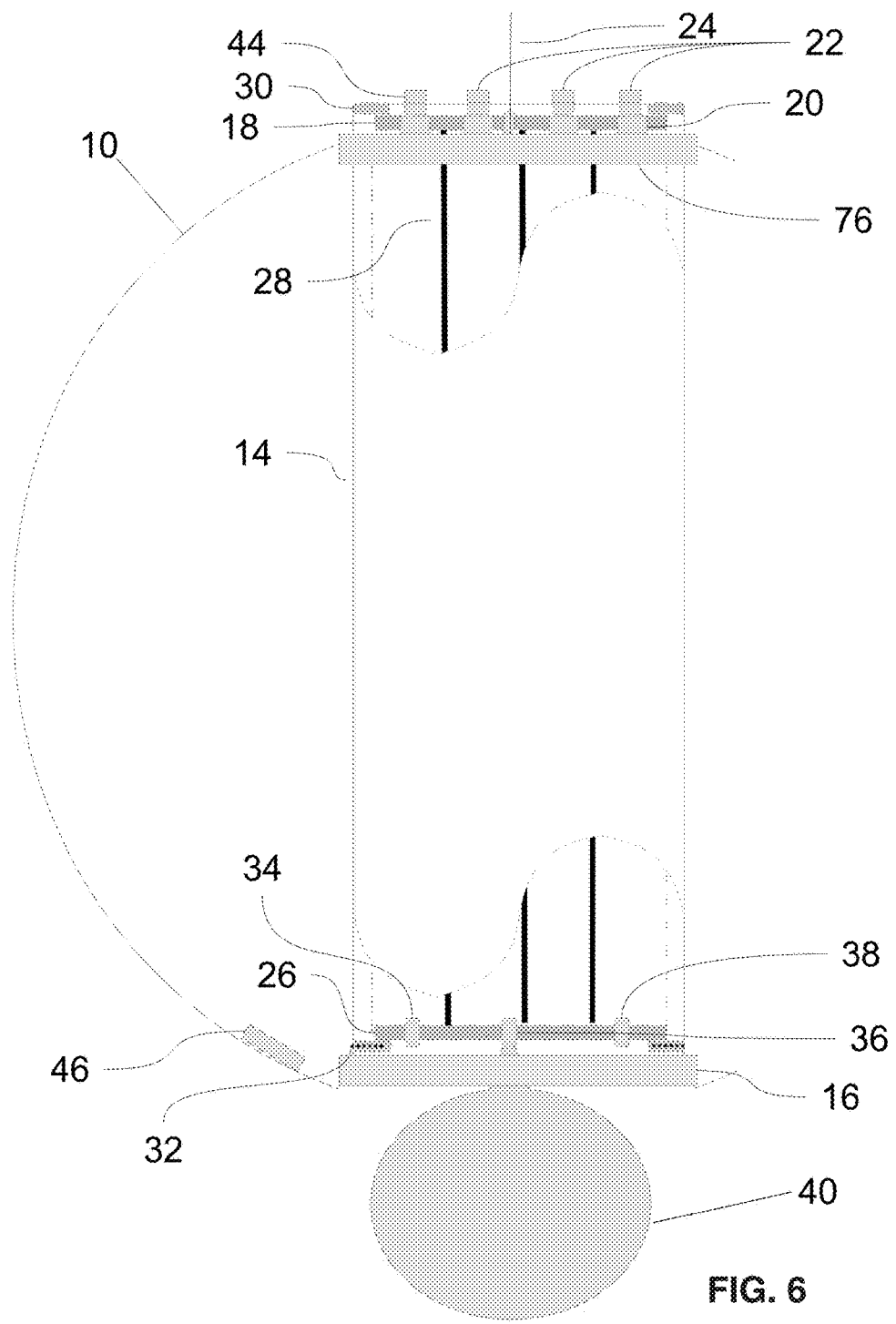
FIG. 6 is a cutaway side view of another embodiment of the shield and instrument capsule in which the shield encloses a volume of water that remains isolated from water outside the shield.

Embodiment of FIG. 6

A further embodiment of a device is shown in FIG. 6. In this embodiment, instrument capsule 14 spans the entire diameter of shield 10. Instrument capsule 14 enters shield 10 through bottom collar 16 and protrudes out of shield 10 through top collar 76. Bottom collar 16 and top collar 76 both provide a liquid tight seal between instrument capsule 14 and shield 10, thereby isolating the water within shield 10 from water outside. In this embodiment of the device, probes 22, electronic signal generator and transmitter 24, and acoustic signal receiver 44 are positioned outside of shield 10.

Operation—Embodiment of FIG. 6

Similarly to the embodiment of FIGS. 1-4, there are three main stages of operation in this embodiment (FIG. 6): 1) pre-deployment preparations; 2) deployment; and 3) retrieval. In addition to the procedures described above for the embodiment FIGS. 1-4, this embodiment (FIG. 6) allows establishment of a controlled volume of water that may be amended or treated with chemical compounds or organisms. Alternatively, the controlled volume of water may contain a known concentration of chemical compound or organisms. In both situations, the controlled volume of water the operator to measure a change in some parameter within the controlled volume of water during deployment of the device. The amendment, measurement, and deployment of the device can be accomplished using a broad range of techniques that suit the interests of the operator.

In FIGS. 7-13, reference numbers refer to features as follows:

101 shell
   102 flotation
   103 aperture
   104 GPS module and antenna
   106 GSM module and antenna
   107 satellite communication module and antenna
   108 radio frequency module and antenna
   109 acoustic signal module and antenna
   110 computer processor
   112 battery
   114 instrumentation capsule
   116 liquid valve
   118 ballast
   120 filter/membrane holders
   122 sensors
   124 sealing gasket
   126 air fill valve
   128 air exhaust port
   130 solenoid valve
   132 water exhaust hole
   134 top end cap
   136 bottom end cap
   138 top retainer ring
   140 bottom retainer ring
   142 retainer set screw
   144 frame
   146 flexible vent tube

Figure 7:
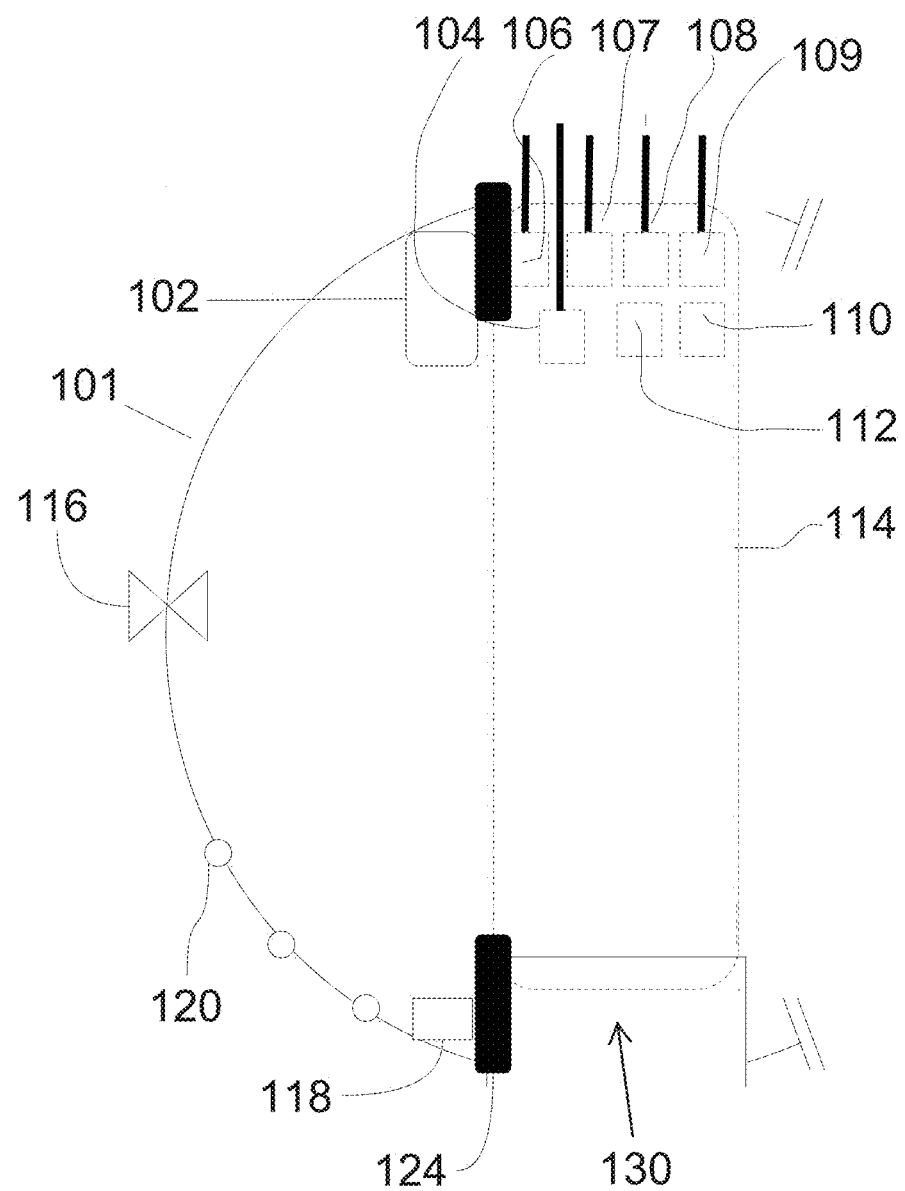
FIG. 7 is a cutaway side view of a device according to at least one embodiment; the right-hand side of the spherical shell is omitted from this and subsequent FIGS. 8-11 for the purposes of illustration clarity.
Figure 8:
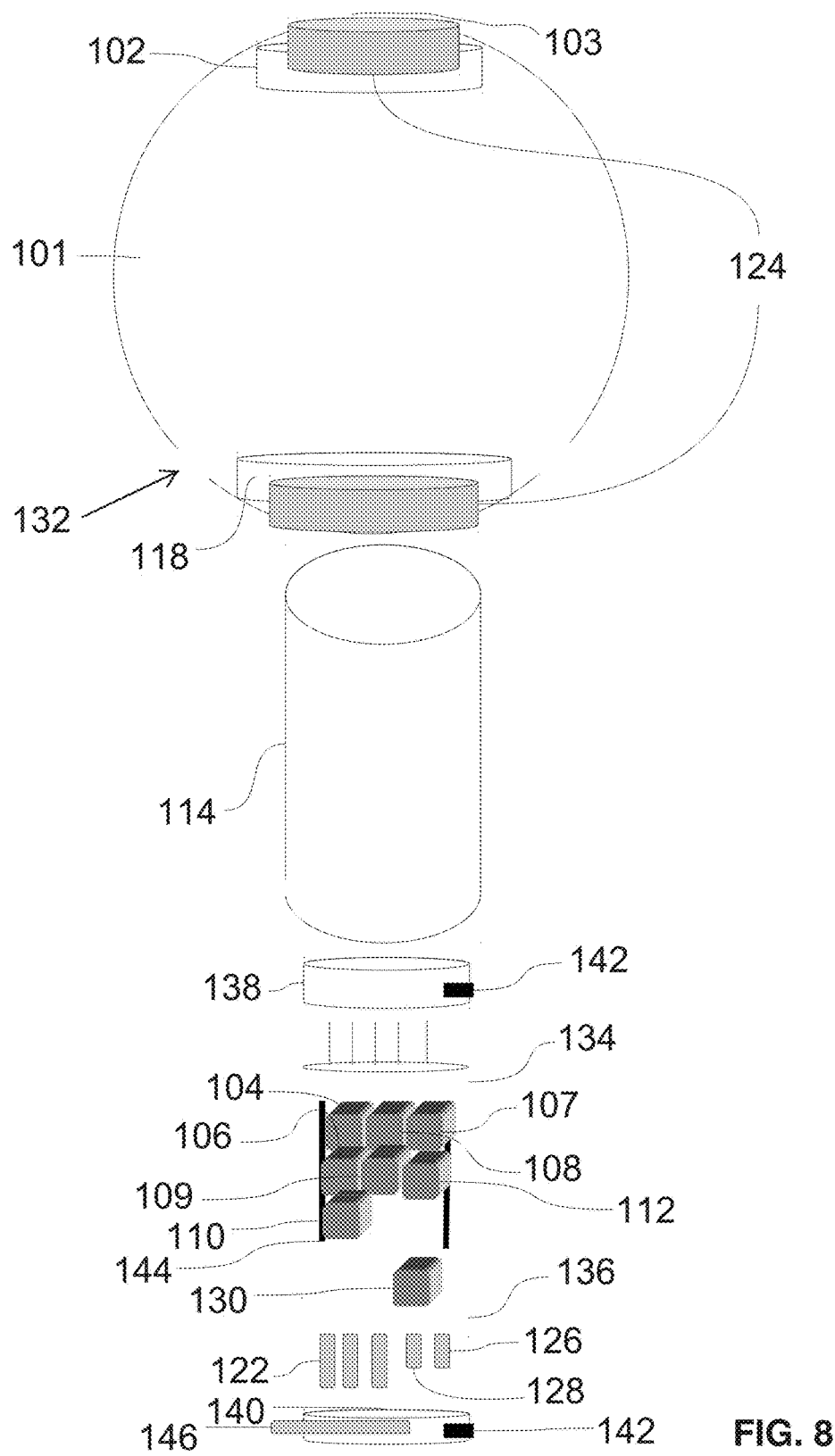
FIG. 8 is an exploded view of another embodiment of a device, some elements of which are identical to those shown in FIG. 10, and some of which are also common to those also shown in FIGS. 7, 9, and 11.

Embodiment of FIGS. 7 and 8

An embodiment of a device is illustrated in FIGS. 7 and 8. A spherical shell 101 constructed of various kinds of clear plastic composite or other material depending on the specific requirements of the research or monitoring being performed. The size of shell 101 can vary with the specific requirements of the research or monitoring being performed. While generally spherical in shape, shell 101 has an aperture 103 in the bottom and the top through which instrument capsule 114 and ballast 118 may be inserted and affixed within shell 101. Instrument capsule 114 is a water-tight compartment containing some or all of the following: Global Positioning System (GPS) module and antenna 104, Global System for Mobile Communication (GSM) module and antenna 106, satellite communication module and antenna 107, radio frequency module and antenna 108, an acoustic signal module and antenna 109; associated antennas pass through water-tight fittings on end cap 134 (FIG. 8) and then exit shell 101 through aperture 103. Adjustable flotation 102 (FIGS. 7 and 8) can be added or subtracted to affect the overall buoyancy of the device, and creates a righting moment that orients the antenna end of the device upwards toward the water surface. Also encased in instrument capsule 114 are a computer processor 110 and battery 112; computer processor 110 can be connected with an external computer. Now referring to FIG. 8, top end cap 134 and bottom end cap 136 serve to seal the electronic equipment inside instrument capsule 114. Top end cap 134 and bottom end cap 136 are ringed by o-rings (not shown) that create pressure-tight seals with the internal wall of instrument capsule 14; these end caps can be inserted and removed. Frame 144 is attached to top end cap 36 and allows a rigid attachment point for the electronics contained within instrument capsule 114. Top retainer ring 138 and bottom retainer ring 140 fit in instrument capsule 114 following insertion of top end cap 134 and bottom end cap 136, respectively. A retainer ring screw 142 secures these retainer rings to the inside of instrument capsule 114, thus trapping top and bottom end caps 134 and 136 in place; the friction of o-rings circling top and bottom end caps 134 and 136 with the internal wall of instrument capsule 114 prevents end caps from slipping towards one another.

Now referring to FIG. 7, liquid valve 116 controls the flow of water into and out of shell 101. A plurality of filter/membrane holders 120 may be included around the circumference of shell 101 to permit exchange of particular solutes or particle sizes between water inside and outside the shell. If configured with filter/membrane holders 120, then a plurality of filters and/or membranes are installed around the circumference of the shell. The filters consist of a porous material with the appropriate pore size to allow particles to move between water inside and outside the shell. To allow solutes and dissolved constituents to move between the inside and outside of the shell, the membranes consist of the appropriate permeable membrane material.

Operation—Embodiment of FIGS. 7 and 8

The operational overview of the embodiment of FIGS. 7 and 8 is provided next. First, with top end cap 134 removed from instrument capsule 114, a person connects an external computer to computer processor 110 and programs the operation of all of the following which are installed within instrument capsule 114: GPS module and antenna 104, GSM module and antenna 106, satellite communication module and antenna 107, radio frequency module and antenna 108, and acoustic signal module and antenna 109. Next, top end cap 134 and affixed electronics is inserted into instrument capsule 114 and top retainer ring 138 is inserted on top of top end cap 134. Retainer set screw 142 is inserted through the wall of top retainer ring 138 and the internal wall of instrument capsule 114. Bottom end cap 136 and bottom retainer ring 140 and set screw 142 are affixed through the opposite end of instrument capsule 114. Before instrument capsule 114 is inserted into shell 101 through aperture 103, the amount of flotation 102 and ballast 118 are adjusted to create the desired amount of buoyancy; flotation 102 consists of non-compressive rings that are positively buoyant and ballast 118 consists of negatively buoyant material, both of which can be added or subtracted in small increments. When positively buoyant, the device may float just below the water surface such that the antennas extend above the water surface (with the exception of acoustic signal module and antenna 109, whose antenna remains submerged even while the device is at the water surface). The position of flotation 102 at the top of the device, which is counter-acted by ballast 118 at the bottom of the device, keeps the orientation of the device in the water stable with instrument capsule 114 oriented vertically above ballast 118. Once inserted through aperture 103, instrument capsule 114 is held in place by sealing gaskets 124, which provide a friction-fit, water-tight connection; in addition, set screws (not shown) can be added through the wall of instrument capsule 114 and the friction-fit sealing gaskets 124 for a stronger mechanical connection.

Still referring to FIG. 7, if filter/membrane holders 120 are present, a person would install the appropriate pore size filter and/or selectively-permeable membranes into filter/membrane holders 120. Next, (whether filter/membrane holders 120 are present or not) the person would then fill the shell with water and associated constituents through valve 116, close the valve, and deploy the device. As an alternative to filling shell 101 with a volume of water for study, bags or containers (not shown) of water and associated constituents may be loaded into shell 101 through aperture 103 prior to insertion of instrument capsule 114. These bags or other containers of water and associated constituents allow isolation and incubation or multiple, discrete samples for study and later analysis. If bags or other containers of water are used, shell 101 must still be filled with water through liquid valve 116 prior to deployment so that the device remains submerged just below the surface (with the exception of antennas that penetrate the water surface).

During deployment, a person monitors the location of the device using either, or a combination of, radio frequency, acoustic signal, or GPS location transmitted via GSM and/or satellite communication transceiver. This position information allows a person locate the device and retrieve it hours or days later, assay the water inside the shell, and connect an external computer to computer processor 110 to download stored data from the GPS module and antenna 104.

Figure 9:
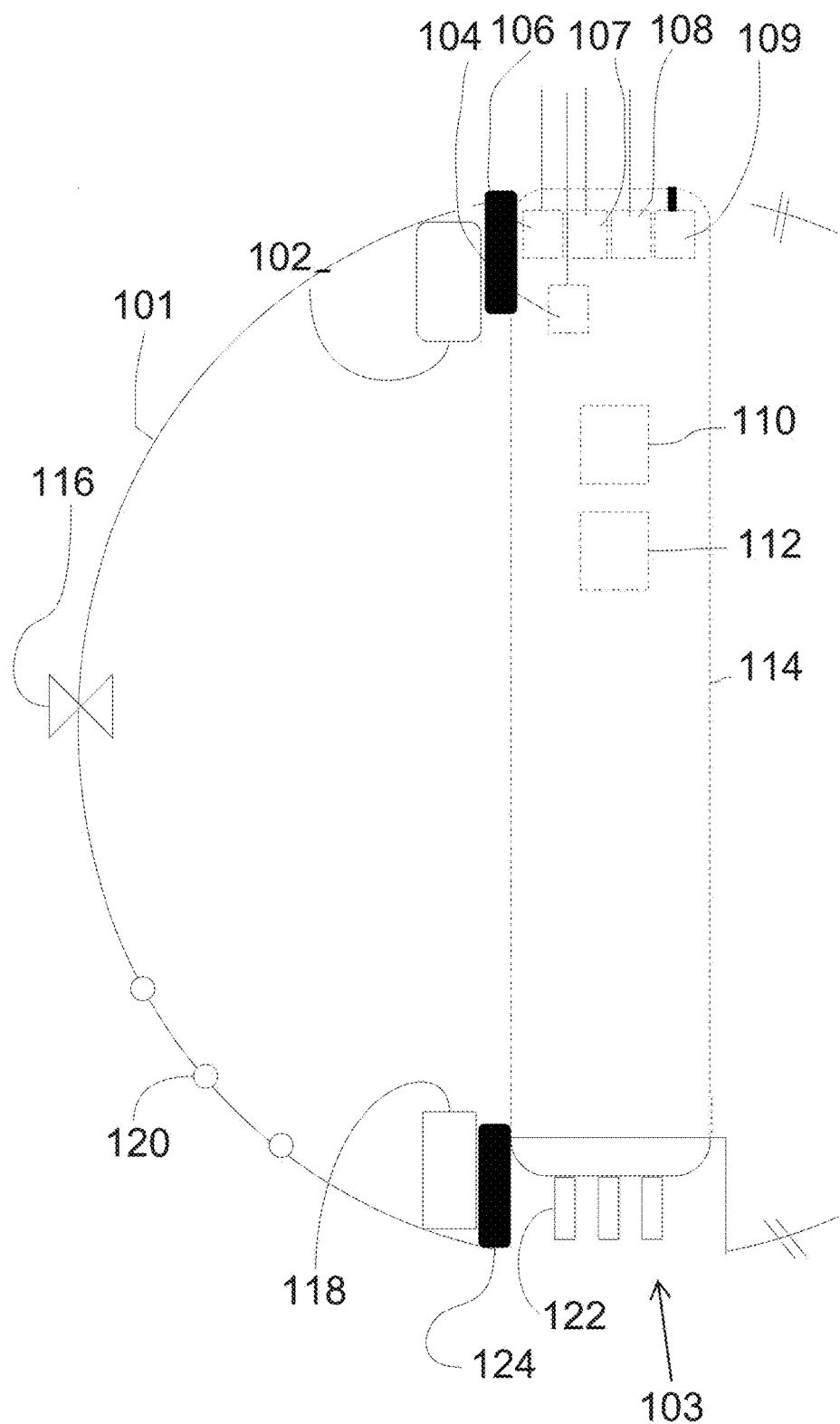
FIG. 9 is a cutaway side view of another embodiment of a device with sensors extending into the surrounding water; many of the elements of this embodiment are similar to those illustrated in FIG. 8.

Embodiment of FIG. 9

Another embodiment of a device is shown in FIG. 9. In this embodiment of the device a plurality of sensors 122 are included for measurement of various environmental variables. These environmental variables may include, but are not limited to, temperature, dissolved oxygen, carbon dioxide, salinity, turbidity, hydrocarbons, nitrate, and chlorophyll. Sensors 122 may include but are not limited to ion-selective probes, membrane-style sensors, fluorometers, spectrophotometers, and other optical instruments. The sensors 122 are controlled by computer processor 110 and powered by battery 112. Signals from the sensors 122 are stored in computer processor 110. The internal cavity of shell 101 can be used to store a volume of water and its associated constituents for study. In this case, filter/membrane holders 120 may be included on shell 101 and liquid valve 116 is included for filling shell 101. The composition of this embodiment of the device is similar in all other respects to that of the embodiment of the device illustrated in FIGS. 7 and 8.

Operation—Embodiment of FIG. 9

Operation of this embodiment is identical to that of that of the embodiment of FIGS. 7 and 8, except that the person may calibrate sensors 122 and program operation of the computer processor 110 before deployment. Calibration of sensors 122 is performed before instrument capsule 114 is inserted into shell 101. Calibration of sensors 122 is performed by connecting an external computer with computer processor 110 and following the sensors' manufacturers' instructions for calibration. Still using an external computer connected with computer processor 110, the person programs the operation of sensors 122. Programming the operation of sensors 122 involves adjusting their frequency of measurement and data storage onto computer processor 110. In this case the device acts as an autonomous sensor platform.

Filter/membrane holders 120 may be present and filters and/or membranes would then need to be installed. Liquid valve 116 may be present so that a person can fill shell 101 with a volume of water and its associated constituents for study. As an alternative to filling shell 101 with a volume of water for study, bags or containers of water and associated constituents may be loaded into shell 101 through aperture 103 prior to insertion of instrument capsule 114. If shell 101 is not filled with water for study, it must still be filled with water through liquid valve 116 prior to deployment so that the device remains mostly below the surface (with the exception of antennas which penetrate the water surface).

Figure 10:
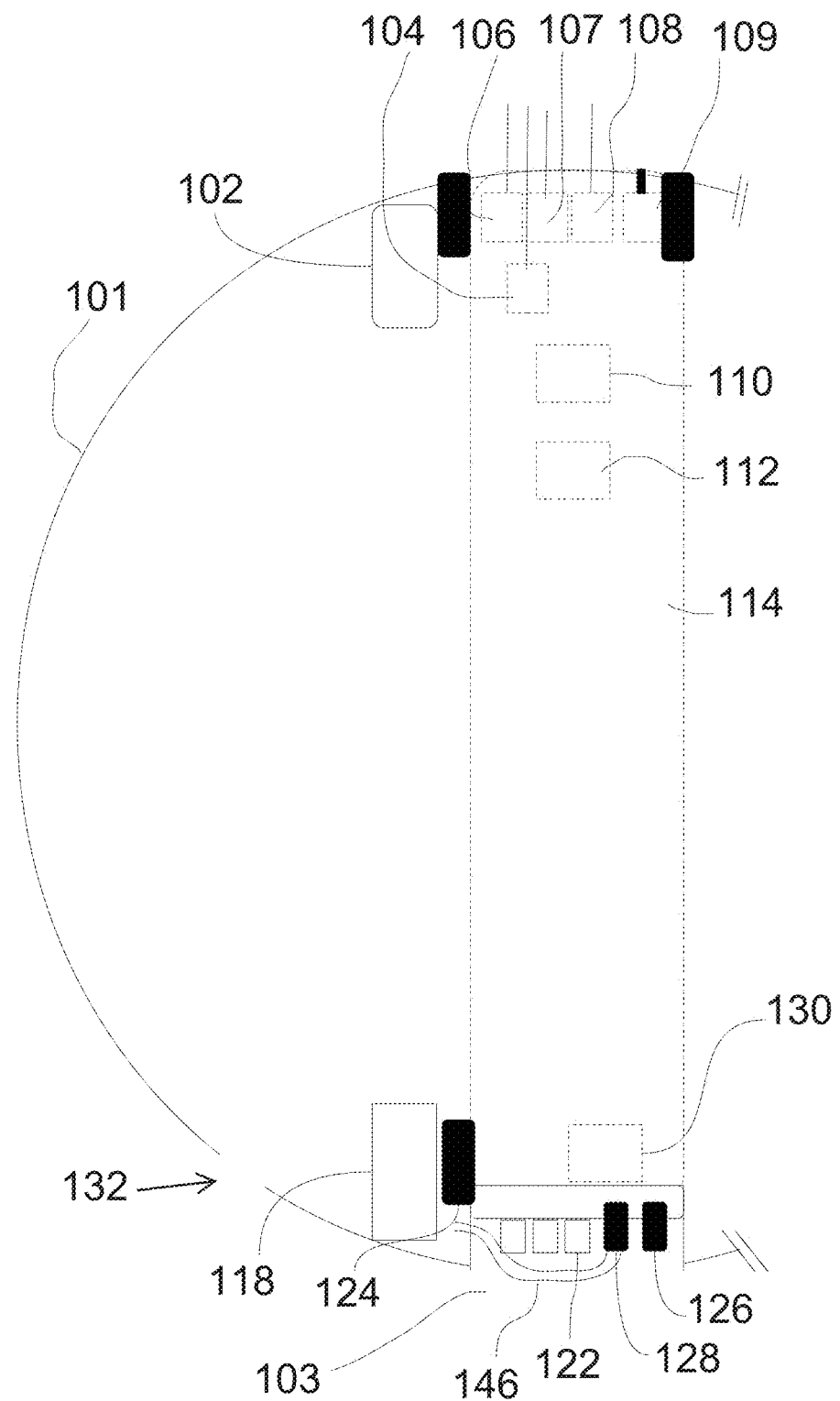
FIG. 10 is a cutaway side view of another embodiment of the device also shown in FIG. 8; this embodiment of the device can travel submerged during operation.

Embodiment of FIGS. 8 and 10

Another embodiment of a device is shown in FIGS. 8 and 10. The composition of the device is generally similar to that described in FIG. 9, except this embodiment is designed to travel submerged during most of its deployment. Air fill valve 126 allows the user to pressurize instrument capsule 114. This pressure can be released through solenoid valve 130 and vented into shell 101 through air exhaust port 128 and flexible vent tube 146. One of the two openings on solenoid valve 130 is exposed to the internal pressure of instrument capsule 114, while the other opening is connected directly to bottom end cap 136 and subsequently air exhaust port 128. Once the normally-closed solenoid valve is opened, the addition of air into shell 101 will force water out through water exhaust holes 132. This air will remain sealed inside shell 101 and provide buoyancy to the device that lifts it to the surface of the water. Once at the surface, GPS, GSM, radio frequency antennas will be capable of sending and receiving signals. The air remains inside shell 101 because of the floating orientation of the device leaves water exhaust holes 132 below the water. As an additional precaution against air escaping through exhaust holes 132 (in the event the orientation of the device is inverted), flaps or valves (not shown) with the proper pressure regulation can be fitted inside exhaust holes 132 which allow water to escape when under pressure by air, but prevent air from escaping.

Operation—Embodiment of FIGS. 8 and 10

Operation of this embodiment combines the elements of operation described for the embodiment of FIG. 7 with elements of operation described for the embodiment described in FIG. 9. The purpose of this embodiment is to drift below the water surface, thus reducing the risk of collision with objects at the surface of the water and to allow sampling throughout the vertical profile of the water. To allow retrieval of the device while submerged, a user first programs computer control device 110 with a time at which to open gas solenoid 130 and vent air into shell 101. Also at this time the user programs the frequency of operation of sensors 122. Next the user pressurizes the instrument capsule using a pump attached to gas fitting 126. The air pressure inside the instrument capsule must exceed the maximum water pressure the device could be potentially exposed to while submerged in order for gas to be expelled when solenoid 130 opens. If this criteria is not met, the pressure of water outside the device would cause water to enter instrument capsule 114 through solenoid valve 130 when opened, negatively impacting the electronics inside.

In summary of the above, the user programs computer control device 110 using an external computer (not shown), calibrates sensors 122, and assembles end caps 134 and 136 and retainer rings 138 and 140, and pressurizes instrument capsule 114 user an external air pump (not shown).

The next step prior to deployment is to adjust the density (mass per volume) of the device. The density of the device can be matched with the density of the surrounding environment to accomplish neutral buoyancy. To accomplish this, the mass and displacement volume of the device are measured, and then the user measures the temperature and salinity of the water to be deployed in. Next the user uses a table of values to determine how much ballast to add or remove from the device to accomplish neutral buoyancy at a given water density. The mass added to the device due to pressurization is calculated from a regression between pressure and mass, and this mass is incorporated into the pre-determined table. The buoyancy of the device will change during deployment if the density of the water it is deployed in changes. The effect of this change in buoyancy on the device's movement through the water is partly dependent on the vertical flow velocity in the water it is deployed in: if the vertical flow velocity induces a vertical force on the device that exceeds the density-dependent buoyancy of the device, than the change in buoyancy will be negated by the hydraulic forces acting vertically through the water column.

With buoyancy adjusted, instrument capsule 114 assembled, pressurized, and inserted into shell 101 through aperture 103, the device is ready for deployment.

Shell 101 is filled with water through water exhaust holes 132. If a controlled volume of water and associated constituents for study was desired to be deployed, this bag or container (not shown) would have been added into shell 101 prior to insertion of instrument capsule 114.

After deployment, the user may track the location of the device using a directional antenna and VHF radio receiver or acoustic signal receiver. The device is retrieved after its pre-programmed surface interval and data from sensors 122 are downloaded from computer processor. If present, bags or containers of water and associated constituents (not shown) are removed and assayed.

As an alternative method of retrieving the device while it is submerged, a hand-held radio or acoustic signaling device (not shown) could be used to send a signal to radio frequency module and antenna 108 or acoustic signal module and antenna 109. Reception of this signal by the device could be programmed to open solenoid valve 130 and vent air into shell 101.

Figure 11:
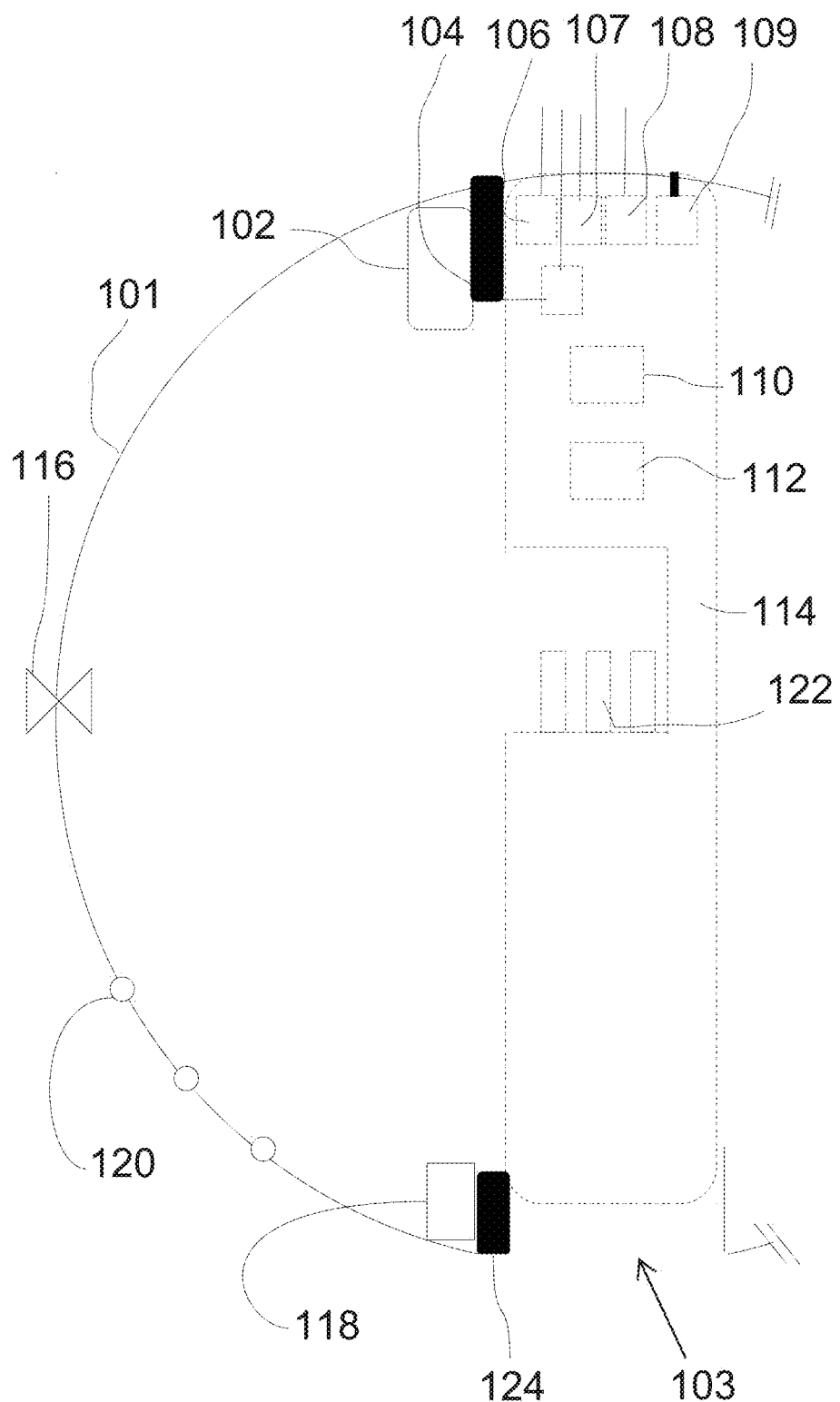
FIG. 11 is a cutaway side view of another embodiment of a device with sensors, which are inside the device, allowing measurement of changes in the properties of water incubated inside the device; many of the elements of this embodiment are similar to those illustrated in FIG. 8.

Embodiment of FIG. 11

A further embodiment of a device is shown in FIG. 11. In this embodiment the device sensors 122 are within shell 101. Filter/membrane holders 120 may be present and liquid valve 116 will be present, allowing a person to fill shell 101 with a volume of water and associated constituents; in this case sensors 122 reflect environmental conditions of the volume of water being stored in shell 101. Composition of the device in this embodiment is largely identical with the embodiment illustrated in FIG. 9.

Operation—Embodiment of FIG. 11

Operation of this embodiment is similar to that described for the embodiment described for FIG. 9 above and elements of operation described for the embodiment presented in FIGS. 7 and 8.

Operation—Orientation Example

Figure 12:
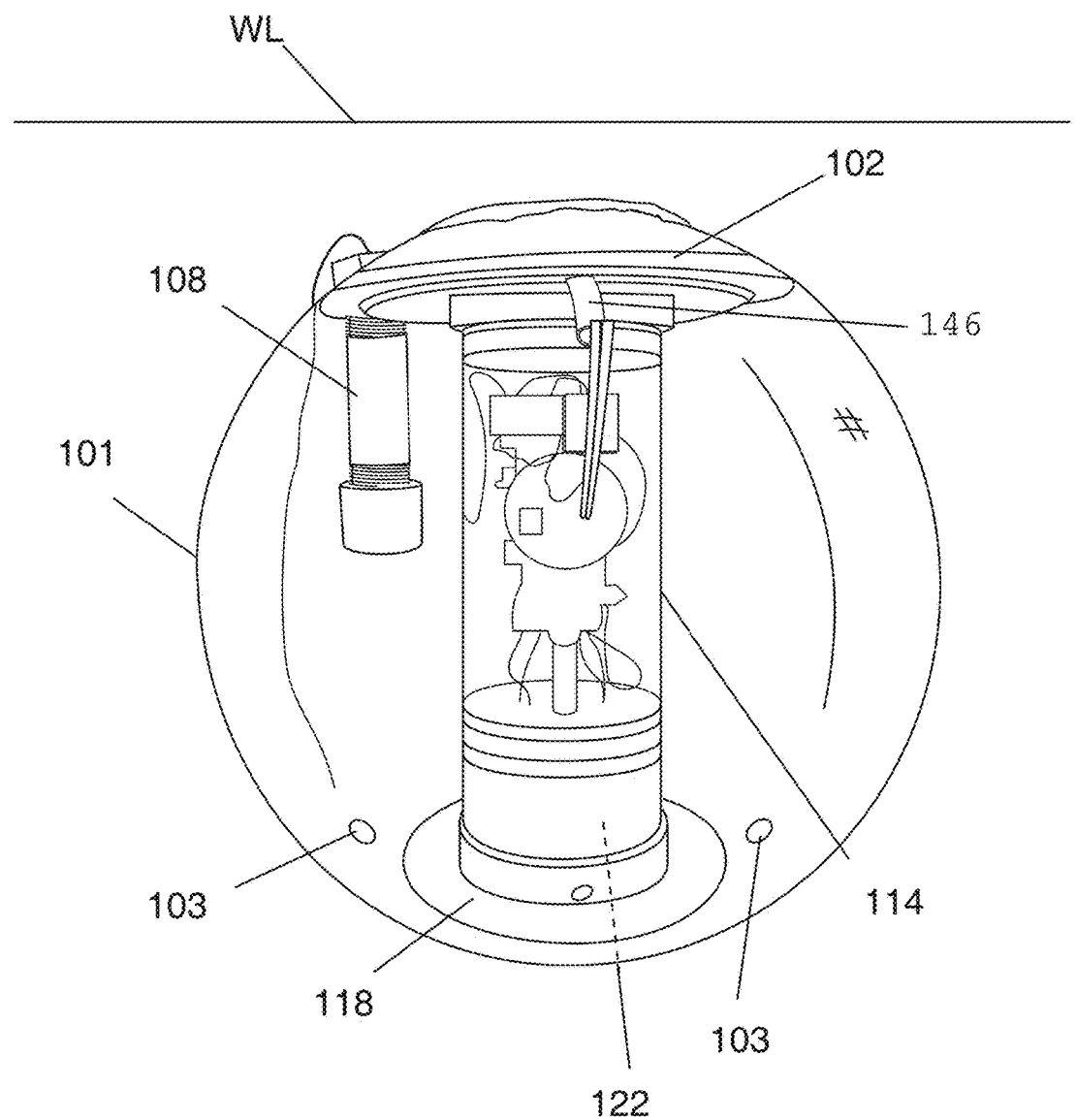
FIG. 12 is a three dimensional view of the device shown in FIG. 8 in a first, submerged position.
Figure 13:
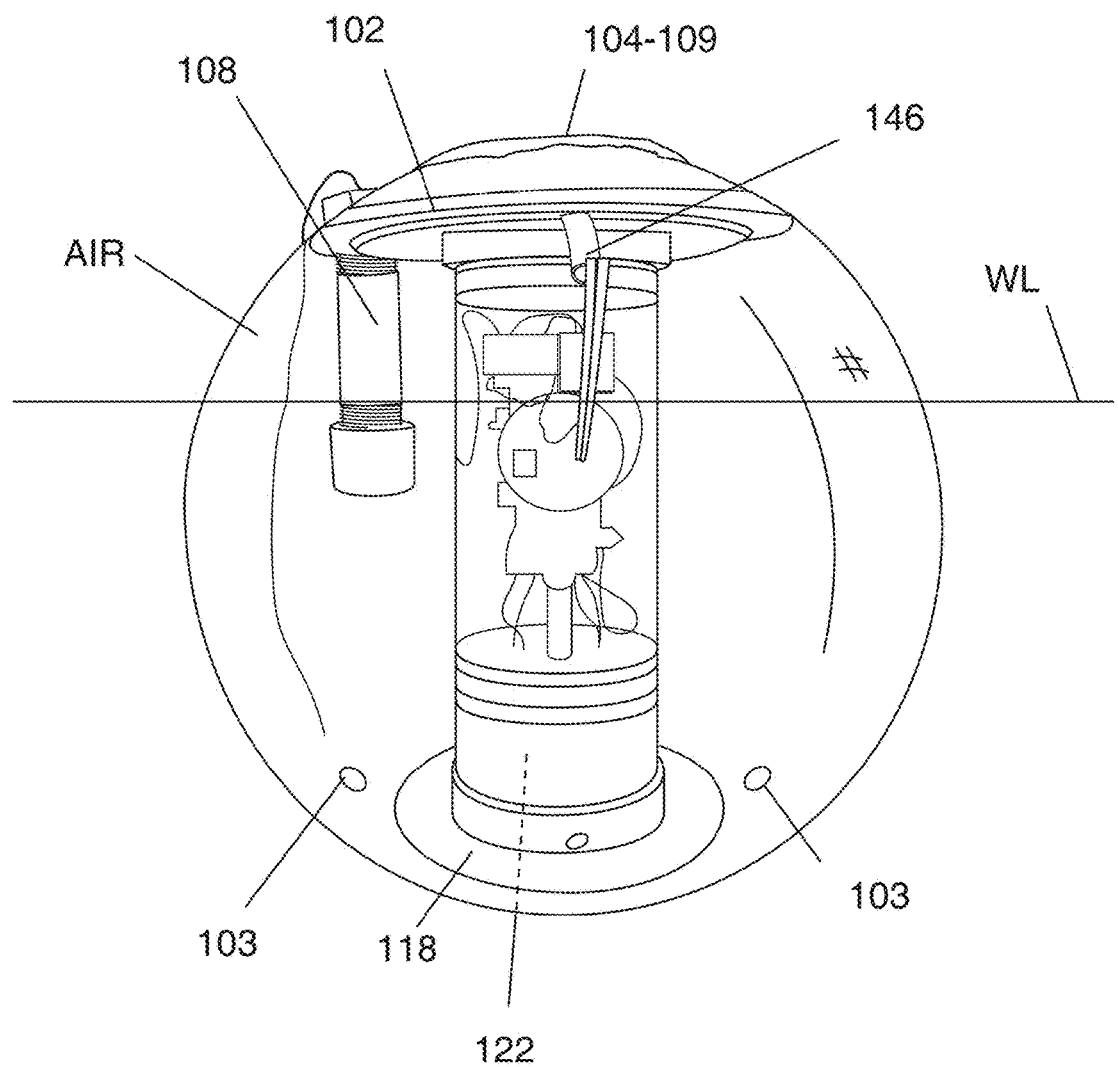
FIG. 13 is a three dimensional view of the device shown in FIG. 8 in a second, buoyant position.

As illustrated in FIGS. 12 and 13, the device of FIGS. 7 and 8 is illustrated, where the device is illustrated submerged in FIG. 12 and buoyant in FIG. 13. As illustrated in FIG. 12, the interior volume of the shield 101 contains liquid, such as river water. In the embodiment illustrated in FIG. 12, compressed air or other gases are contained within the instrument capsule 114 and the total density of the device (including the shield 101 and the instrument capsule 114) is greater than or equal to the density of the liquid in which the device is placed. The computer control module then directs a pump or valve to release the compressed air from within instrument capsule 114 through vent tube 146 into the interior volume of the shield 101. With the center of gravity of the device being located towards the ballast 118 and sensors' 122 end of the shield 101 when the device is submerged, expulsion of water from apertures 103 by the compressed gas causes the device to float with antennas 104 through 109 facing upwards and above the water line "WL." So long as the apertures 103 are positioned below the water line WL, air cannot escape shield 101 and the device will remain floating indefinitely. As illustrated, air (designated AIR in the drawings) collects within an upper facing portion of an inner surface of the shield and maintains the device at least partially above the water line WL. At this point, the device is retrieved by an operator. The device may emit a signal indicative of location for re-capture by the operator.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

What is claimed is:

1. A portable free drifting device for measuring environmental parameters of water, the device comprising:
    a shield;
    a supply of compressed gas and a valve;
    an instrument capsule coupled with the shield;
    a computer control system contained within the instrument capsule configured to direct:
        at least one electronic sensor to measure one or more of chemical, physical, hydrological, and biological properties of water surrounding the shield; and
        the valve to release a portion of gas from the supply of compressed gas into the shield to alter the envelope density of the device;
    a signal generator for transmitting a location of the device to a remote receiver;
    a ballast of adjustable mass within the device that alters the density of the device;
    wherein an aperture is defined in the shield for:
        allowing water into the shield and air out of the shield when the device is submerged underwater and inverted by a user deploying the device; and
        allowing, when the portion of gas is released and thereby vented into the shield and collected in the shield, water displaced by the portion of gas to be forced out of the shield; and
    whereby the device is deployed in a water body and measures a parameter of water for a predetermined period of time, after which the device is directed to the water surface,
    wherein the aperture permits placement of one or more containers of water and associated constituents within the shield which traps the one or more containers when the instrument capsule is received in the shield; and
    wherein the water inside the one or more containers before the device is deployed is differentiable from the water inside the one or more containers after the device is retrieved.

2. The device of claim 1, further comprising-a plurality of sensors that provide signals to the computer control system and allow it to compute water depth and density.

3. The device of claim 1, wherein the shield is generally spherical.

4. The device of claim 1, further comprising:
    a signal receiver and receiver antenna configured for receiving controlling information for the computer control system via a remote signal,
    wherein the antenna is positioned at one end of the device and oriented upwards when the device is more buoyant than the water surrounding therein.

5. The device of claim 1, wherein the aperture is fitted with a valve for controlling the ingress and egress of water within the shield.

6. The device of claim 5, wherein at least one electronic sensor for measuring one or more of chemical, physical, hydrological, and biological properties of water is located inside the shield.

7. The device of claim 1, wherein at least one electronic sensor for measuring one or more of chemical, physical, hydrological, and biological properties of water is located inside the shield.

* * * * *